(12) United States Patent
Stradiotto et al.

(10) Patent No.: US 7,696,183 B2
(45) Date of Patent: Apr. 13, 2010

(54) IBANDRONATE SODIUM PROPYLENE GLYCOL SOLVATE AND PROCESSES FOR THE PREPARATION THEREOF

(75) Inventors: David A. Stradiotto, Brantford (CA); Allan W. Rey, Brantford (CA); Probal Kanti Datta, Hamilton (CA); Krista Lyn Traynor, Brantford (CA); Cameron L. McPhail, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 11/639,204

(22) Filed: Dec. 15, 2006

(65) Prior Publication Data

US 2008/0139508 A1    Jun. 12, 2008

(30) Foreign Application Priority Data

Dec. 12, 2006    (CA)    ................................. 2570949

(51) Int. Cl.
*A61K 31/663*    (2006.01)

(52) U.S. Cl. ...................................... 514/102
(58) Field of Classification Search ........................ None
See application file for complete search history.

(56) References Cited

U.S. PATENT DOCUMENTS

| 3,970,651 | A | 7/1976 | Kaplan et al. |
| 4,091,213 | A | 5/1978 | Kaplan et al. |
| 4,927,814 | A | 5/1990 | Gall et al. |
| 5,908,959 | A | 6/1999 | Kubela et al. |
| 6,143,326 | A | 11/2000 | Mockel et al. |
| 6,294,196 | B1 | 9/2001 | Gabel et al. |
| 6,468,559 | B1 | 10/2002 | Chen et al. |
| 6,977,243 | B2 | 12/2005 | Li et al. |
| 7,105,179 | B2 | 9/2006 | Li et al. |
| 2004/0019211 | A1 | 1/2004 | Remenar et al. |
| 2005/0267302 | A1 | 12/2005 | Barton et al. |
| 2006/0052432 | A1 | 3/2006 | Remenar et al. |
| 2006/0172975 | A1 | 8/2006 | Eiermann et al. |
| 2006/0223794 | A1 | 10/2006 | Bourghol Hickey et al. |
| 2007/0015841 | A1* | 1/2007 | Tawa et al. ................... 514/738 |
| 2007/0161606 | A1* | 7/2007 | Bayer et al. ................. 514/102 |

FOREIGN PATENT DOCUMENTS

| CA | 1101840 | 5/1981 |
| JP | 105813/75 | 8/1975 |
| JP | 1-290682 | 11/1989 |
| WO | WO 2004/060347 A2 | 7/2004 |
| WO | WO 2005/063779 A2 | 7/2005 |
| WO | WO 2006/002348 A2 | 1/2006 |
| WO | WO 2006/024024 A2 | 3/2006 |

* cited by examiner

*Primary Examiner*—Daniel M Sullivan
*Assistant Examiner*—Yevegeny Valenrod

(57) ABSTRACT

A novel form of Ibandronate sodium which is particularly suitable for pharmaceutical applications, and a process for preparing said novel form.

7 Claims, 3 Drawing Sheets

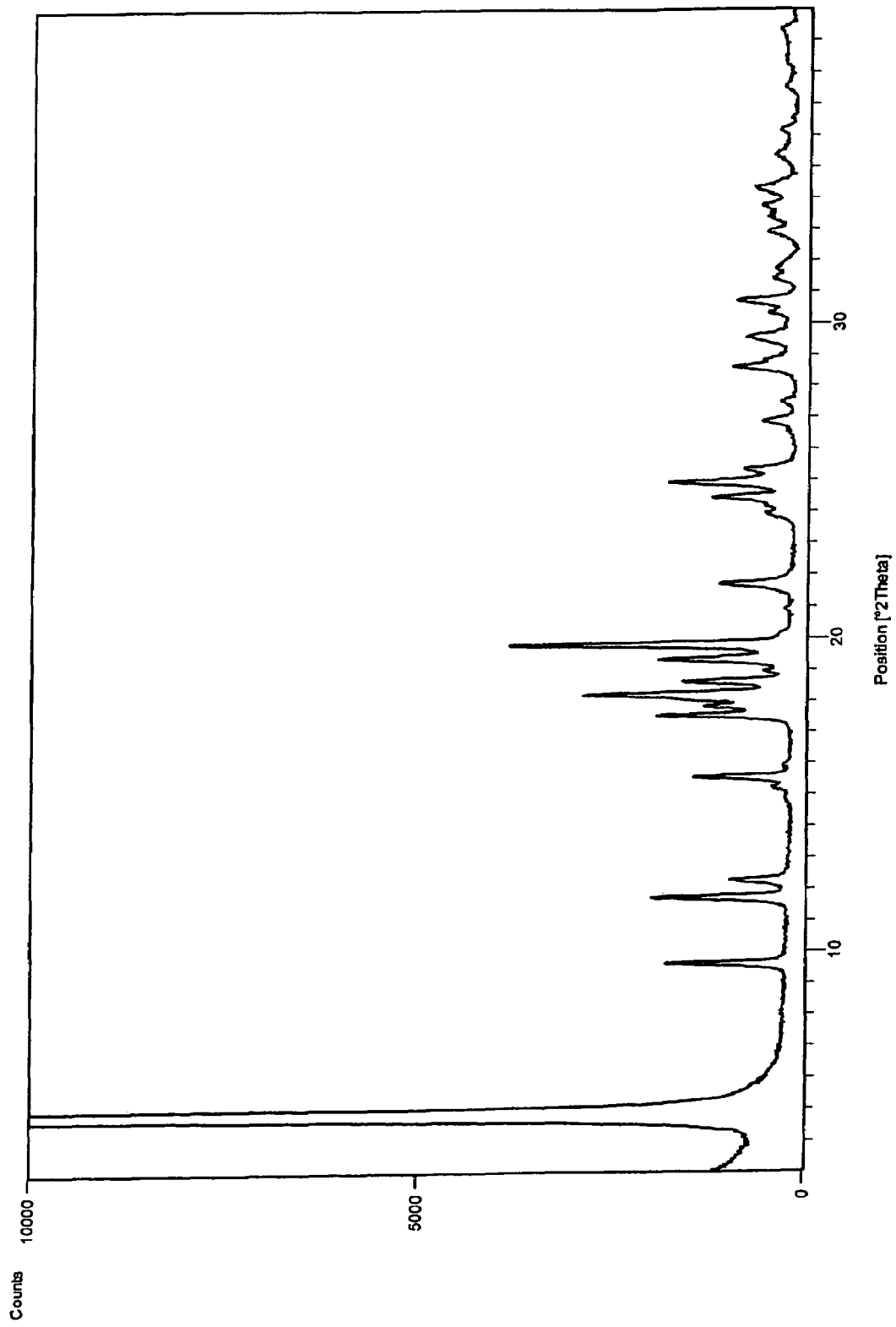
Figure 1 – PXRD Diffractogram (using CuKα radiation)

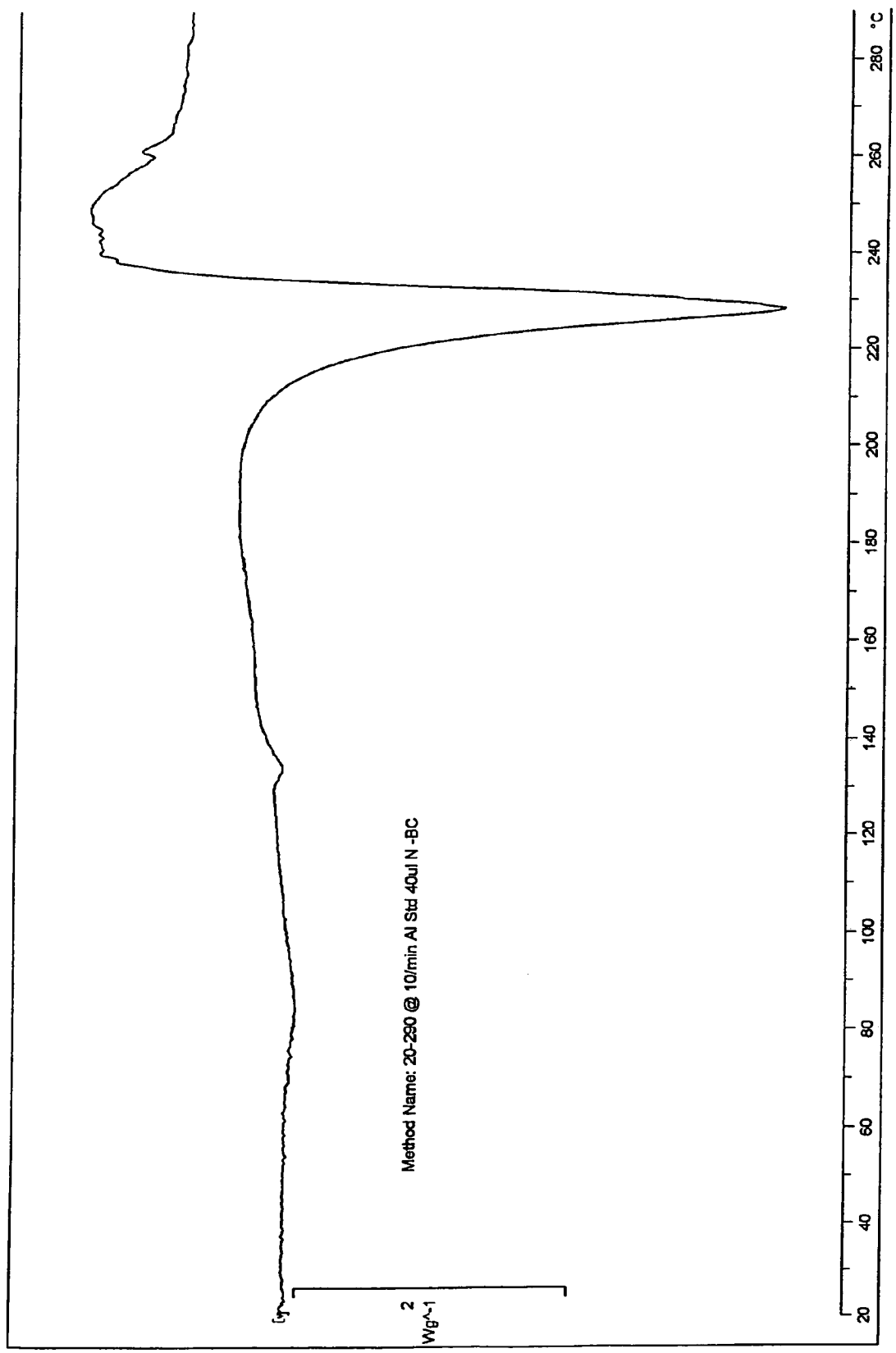
Figure 2 – DSC Thermogram

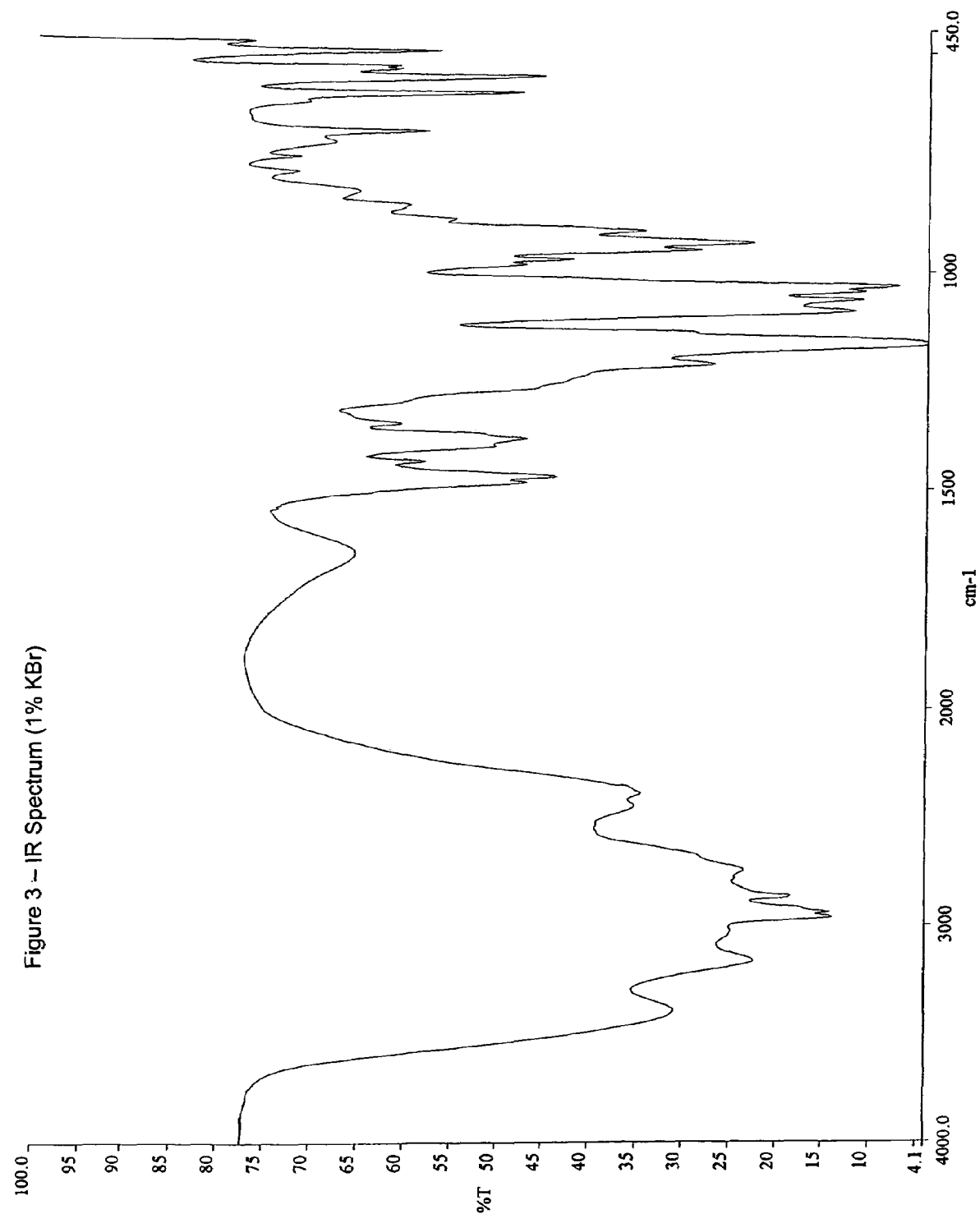
Figure 3 – IR Spectrum (1% KBr)

IBANDRONATE SODIUM PROPYLENE GLYCOL SOLVATE AND PROCESSES FOR THE PREPARATION THEREOF

FIELD OF THE INVENTION

The present invention relates to a new solvated form of Ibandronate sodium (Boniva®) by formation of a 1:1 Ibandronate sodium propylene glycol solvate, and a method for its preparation. This form is particularly well-suited for pharmaceutical applications.

BACKGROUND OF THE INVENTION

Ibandronate sodium (1,3-(N-methyl-N-pentyl)amino-1-hydroxypropane-1,1-diphosphonic acid, monosodium salt) is a third-generation member of the bis-phosphonate class of drugs effective for the treatment of bone disorders such as osteoporosis. It is marketed under the brand name Boniva® and its mode of action is to inhibit osteoclast-mediated bone resorption. An advantage of this pharmaceutical is that it can be used as a once-monthly treatment.

FIG. 1, Ibandronate Sodium (Boniva®)

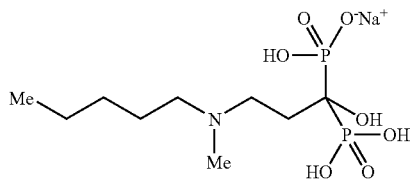

The use of Ibandronate sodium as a medicine was originally disclosed in U.S. Pat. No. 4,927,814 assigned to Boehringer Mannheim GmbH. This patent teaches the use of various structurally related diphosphonic acid derivatives, including Ibandronic acid, for the treatment of various bone-disorders. This patent also teaches the physiologically active salts of these diphosphonic acids, in particular their mono- or dialkali metal salts and states that these alkali metal salts can usually be readily purified by reprecipitation from water/methanol or from water/acetone.

WO 2005/063779 (Lyogen) discloses improved processes to prepare diphosphonic acids, in particular Risendronic, Zoledronic and Ibandronic acids. It also discloses an amorphous form of Ibandronate sodium. In contrast to the prior art, this patent application teaches the use of phosphorus oxychloride and phosphorous acid in a well-defined ratio to obtain a fluid mass that was stirrable throughout the reaction. Similarly, U.S. Pat. No. 5,908,959 (Apotex Inc.) resolved stirring issues related to another diphosphonic acid, Alendronic acid and its salts, by performing the phosphorylation reaction in the presence of polyethylene glycol.

US patent application 2006/0172975 (Hoffmann-La Roche) describes Ibandronate sodium monohydrate Form A and Form B.

WO 2006/024024 (Teva) teaches solid amorphous and crystalline forms of Ibandronate sodium which are often full or partial solvates and hydrates. Various primary alcohols are listed as possible solvating agents including ethanol and butanol. Of note is that many of the types of solvating agents are toxic at higher doses and therefore would have to be removed before they could be used as an active ingredient. To this end, there are well-recognized international guidelines regarding the amount of residual solvent permissible in active ingredients [ICH Q3C(R3) in http://www.ich.org/LOB/media/MEDIA423.pdf].

Teva application WO 2006/024024 also teaches that common liquid carriers such as propylene glycol can be used to suspend or dissolve their active forms of Ibandronate sodium and solid excipients for liquid pharmaceutical compositions. This application, however, does not contemplate the novel propylene glycol solvate form of the present invention.

The use of propylene glycol as a solvating agent for certain pharmaceuticals is known, for instance Celecoxib (US 2006/0052432), Olanzapine (US 2006/0223794), Eplerenone (US 2005/0267302), Azithromycin (U.S. Pat. No. 7,105,179) and Cephalosporin derivatives (U.S. Pat. No. 4,091,213). However, the use of propylene glycol for the diphosphonate class of drugs, including Ibandronate sodium, is unknown.

Another patent application by Teva, WO 2006/002348, discloses various routes to Ibandronic acid and various crystalline and amorphous forms of Ibandronic acid. This application also teaches the benefits of propylene glycol as a carrier for liquid pharmaceutical compositions of ibandronic acid, but does not contemplate the novel Ibandronate sodium propylene glycol solvate of the present invention.

There are various patents which disclose formulation improvements in order to minimize well-known tolerability problems associated with the diphosphonate class of drugs. For instance, U.S. Pat. No. 6,143,326 (Roche Diagnostics) and U.S. Pat. No. 6,294,196 (Hoffmann-La Roche), relate to the outer coat of the tablets containing Ibandronate sodium in order to obtain the desired release profile.

Another patent is U.S. Pat. No. 6,468,559 (Lipocine) which describes an effective oral dosage form of many bisphosphonates (14), including Ibandronic acid and salts, using enterically coated capsules comprised of the active and a pharmaceutically acceptable, substantially non-aqueous liquid or semi-solid carrier in which the active agent is dissolved or suspended. There are numerous examples (>200) of the non-aqueous carriers mentioned in U.S. Pat. No. 6,468,559 including propylene glycol. In the teachings of this patent, the active is dissolved or suspended in the liquid carriers, but is not made into, or isolated as, a solvate.

Given the difficulties associated with finding suitable processes to and forms of Ibandronate sodium, new and industrially acceptable solutions, which offer advantages relative to the prior art, were required.

SUMMARY OF THE INVENTION

During our process optimization work to find novel, cost-effective and robust synthetic procedures to Ibandronate sodium and improved forms of the active ingredient, we surprisingly discovered that a diol, namely propylene glycol (1,2-propanediol), forms a crystalline 1:1 solvate with Ibandronate sodium that can be easily purified and, thereafter, formulated into effective dosage forms.

The use of propylene glycol as a solvating agent has many advantages. These include that it is inexpensive and widely-available, having many industrial applications including use as a moisturizer for medicines, cosmetics, food and tobacco products and as a humectant food additive. Furthermore, it has an established safety and can be purchased as pharmaceutically acceptable NF-grade material. For instance, it is listed as a Food Additive in FDA's "Everything" Added to Food in the United States (EAFUS)" database (http://www.cfsan.fda.gov/~dms/eafus.html).

The Ibandronate sodium propylene glycol solvate of this invention is easily made and crystalline. This form has many desirable characteristics including that it is non-hygroscopic, free-flowing, and is chemically and polymorphically stable. Another benefit is that it is easily dried, even on industrial scale, since it retains very little residual solvent.

Propylene glycol can be obtained in either enantioenriched R or S form or as a mixture of enantiomers (i.e., as a racemate). The latter racemate form of propylene glycol is more preferred for this invention.

In another aspect of the invention, the phosphorylation of 3-(N-methyl-N-pentylamino)propanoic acid (or its hydrochloride salt) using phosphorous acid and phosphorous trichloride in the presence of polyethylene glycol led to superior results. Most significantly, it allowed for the reaction to be accomplished with effective stirring throughout thereby permitting facile and safe scale-up to industrial levels.

BRIEF DESCRIPTION OF THE DRAWINGS

FIG. 1 illustrates a powder x-ray diffraction pattern of ibandronate sodium propylene glycolate.

FIG. 2 illustrates a DSC thermogram of crystalline ibandronate sodium propylene glycolate.

FIG. 3 illustrates an IR spectrum of ibandronate sodium propylene glycolate.

DETAILED DESCRIPTION OF THE INVENTION

The solvated form of Ibandronate sodium may be formed in various ways. For instance, Ibandronate sodium can be dissolved in water at about 30° C. to about 100° C., more preferably at about 50° C. to about 80° C. Typically this requires about 3 volumes of water relative to the weight of the Ibandronate sodium. This is followed by the addition of about 0.5 to 2 volumes of propylene glycol and the solution is cooled at about −5° C. to about 30° C., more preferably at about 0° C. to about 20° C., most preferably at about 0° C. to about 5° C. The material is isolated by filtration and rinsed with an organic solvent selected from a C3 to C5 ester, most preferably ethyl acetate or a C3 to C6 alkyl ketone, most preferably acetone, or a C4 to C8 cyclic or acyclic ether, most preferably tetrahydrofuran. This last step is done to remove the excess propylene glycol.

The Ibandronate sodium propylene glycolate prepared by this method can be characterized by a PXRD pattern having characteristic peaks expressed in angle 2-theta at approximately:

| Angle 2-theta | Intensity % |
|---|---|
| 9.7 | 0.24 |
| 11.8 | 0.49 |
| 18.3 | 0.86 |
| 19.4 | 0.57 |
| 19.8 | 0.83 |
| 24.5 | 0.59 |

The Ibandronate sodium propylene glycolate prepared by this method can be further characterized by a PXRD pattern as shown in FIG. 1.

The Ibandronate sodium propylene glycolate prepared by this method can be characterized by a DSC having a major endotherm at a peak onset temperature of about 220° C. and a peak maximum of about 228° C. The crystalline Ibandronate sodium propylene glycolate prepared by this method can be further characterized by a DSC thermogram as shown in FIG. 2.

The Ibandronate sodium propylene glycolate prepared by this method can be characterized by its IR spectrum (1% KBr) having characteristic peaks expressed in cm$^{-1}$ at approximately:

| IR band (cm$^{-1}$) | % Transmission |
|---|---|
| 3382 | 31 |
| 2385 | 34 |
| 1467 | 42 |
| 1380 | 46 |
| 1162 | 3.2 |
| 1032 | 4.8 |
| 931 | 20 |

The Ibandronate sodium propylene glycolate prepared by this method can be further characterized by an IR spectrum (taken in 1% KBr) as depicted in FIG. 3.

In another embodiment of the invention, the Ibandronate sodium is directly isolated by addition of propylene glycol to a mixture of Ibandronic acid in a substantially aqueous media, adjusting the pH to about 4 to about 5 and then adding about 0.5 to about 2 volumes propylene glycol. The solution is cooled at about −5° C. to about 30° C., more preferably at about 0° C. to about 20° C., most preferably at about 0° C. to about 5° C. The material is isolated by filtration and rinsed with an organic solvent selected from a C3 to C5 ester, most preferably ethyl acetate or a C3 to C6 alkyl ketone, most preferably acetone, or a C4 to C8 cyclic or acyclic ether, most preferably tetrahydrofuran. This last step is done to remove the excess propylene glycol.

In another embodiment of the invention, an improved procedure for the phosphorylation of 3-(N-methyl-N-pentylamino)propanoic acid (or its hydrochloride salt) was accomplished using phosphorous acid and phosphorous trichloride in the presence of polyethylene glycol media. This permitted the reaction to be accomplished with effective stirring throughout and was easily scaled, in a safe manner, to multikilo levels. The most performed average molecular weight of polyethylene glycol was about 400 g/mol. The amount of phosphorous acid and phosphorous trichloride relative to the 3-(N-methyl-N-pentylamino)propanoic acid substrate was about 0.8 to about 2.0 equivalents, more preferably about 1.0 to about 1.6 equivalents. The preferred temperature for performing the reaction was about 45 to about 70° C., more preferably at about 55 to about 60° C. The most preferable amount of polyethylene glycol was about 0.8 to about 2 volumes, relative to the weight of the 3-(N-methyl-N-pentylamino)propanoic acid substrate. This reaction is also preferably performed in the presence of a co-solvent, most preferably toluene. The preferred amount is about 2 to about 4 volumes, relative to the weight of the 3-(N-methyl-N-pentylamino)propanoic acid substrate.

The following examples are representative of the present invention and are not intended to be limiting.

EXAMPLE 1

Preparation of Sodium Ibandronate propylene glycolate from 3-(N-methyl-N-pentylamino)propanoic acid hydrochloride 3-(N-Methyl-N-pentylamino)propanoic acid hydrochloride (100 g) was suspended in toluene (300 mL) and polyethylene glycol 400 (120 mL). Phosphorous acid (43.01 g 1.1 eq.) was added to the mixture. The mixture was warmed and phosphorous trichloride (98.22 g, 1.5 eq.) was added at a rate such that the temperature remained below 60° C. The mixture was stirred for 10 hours at 55-60° C. whereupon it was quenched by adding water (450 mL). The water addition was controlled to maintain a reaction temperature below 70° C. The layers were separated and the aqueous layer was refluxed for 6 hours. The mixture was cooled to 40-45° C. to provide Ibandronic acid in solution and the pH was adjusted to 4.3-4.5 using 50% aqueous sodium hydroxide. Propylene glycol (150 mL) was then added to the reaction mixture at 60-65° C. and stirred for 4-5 hours. The mixture was cooled to 20-25° C. over a period of 2-3 hours and then for 3-4 hours at 0-5° C., filtered, washed with acetone (2×150 mL) and dried in vacuo.

Sodium Ibandronate (145 g) from above was suspended in 363 mL (2.6 vol) of water in a round bottom flask. The flask was heated to dissolution (60-65° C.) whereupon propylene glycol (72 mL) was added to the flask and held at this temperature for 6 hours. The flask was cooled to 20-25° C. and then 0-5° C. and held at this temperature for 3 hours. The precipitated solid was isolated by filtration and rinsed with ethyl acetate (2×200 mL). The damp filter caked was then stirred with ethyl acetate (650 mL) for 3 hours at 40-45° C., isolated by filtration and dried in a vacuum oven at 60-65° C. This provided 110.3 grams of Ibandronate sodium propylene glycolate.

Sodium Ibandronate propylene glycolate having the following analytical characteristics was obtained.

$^1$H-NMR (400 MHz; D$_2$O): δ=3.90-3.82 (1H, m); 3.59-3.50 (2H, m), 3.45-3.40 (1H, m), 3.36-3.30 (1H, m), 3.27-3.18 (1H, m), 3.07-3.01, (1H, m), 2.84 (3H, s), 2.44-2.26 (2H, m), 1.74-1.68 (2H, m), 1.35-1.29 (4H, m), 1.13 (3H, d, J=6.7 Hz), 0.88 (3H, t, J=6.9 Hz). $^{13}$C-NMR (100 MHz, D$_2$O): δ=75.0 (t, J=135.4 Hz), 70.6, 69.3, 59.0, 55.6 (t, J=6.8 Hz), 42.1, 30.64, 30.55, 25.9, 24.2, 20.8, 15.8. Mass Spectroscopy (m/z, ES$^-$): 318 (M-Na, 100). Elemental Analysis: Calculated for C$_{12}$H$_{30}$O$_9$NNa; C 34.54; H 7.25; N 3.36. Found: C 34.44; H 7.56; N 3.33. IR (1% KBr): 3382, 3160, 2962, 2863, 2385, 1482, 1468, 1381, 1344, 1210, 1162, 1090, 1063, 1032 cm$^{-1}$.

EXAMPLE 2

Preparation of Sodium Ibandronate propylene glycolate from Ibandronic acid

Ibandronic acid (6.30 g, 19.7 mmol) was suspended in water (18.0 mL) and heated to dissolution (42° C.). The pH was adjusted to 4.4 using 50% aqueous sodium hydroxide. 1,2-Propanediol was added to the reaction mixture at 56° C. and the mixture was stirred for 2.5 hours. The mixture was cooled to 20-25° C. over a period of 2.5 hours and stirred for another 15 hours. The mixture was filtered, washed with ethyl acetate (2×10 mL). The damp solid was suspended in 30 mL of ethyl acetate and stirred at 20-25° C. for 1 hour, filtered, rinsed with ethyl acetate (2×10 mL) and dried in vacuo at 65° C. for 8 hours to yield sodium Ibandronate propylene glycolate (4.54 g).

EXAMPLE 3

Preparation of Sodium Ibandronate R-Propylene Glycolate by recrystallization

Sodium Ibandronate (2.0 g) was suspended in 6 mL (3.0 vol) of water in a round bottom flask. The flask was heated to dissolution (55-65° C.) at which point 2 mL R-propylene glycol (1.0 vol) was added to the flask. The temperature of the flask was held at 60-65° C. for 2 hours, then cooled to 20-25° C. and held at this temperature for 0.5 hours. Acetone (4 mL, 2.0 vol) was added and the flask was stirred at 20-25° C. for 0.5 hours. The precipitated solid was isolated by filtration, rinsed with acetone and dried in a vacuum oven at 60-65° C. This provided 1.97 grams of Ibandronate sodium R-propylene glycolate.

EXAMPLE 4

Preparation of Sodium Ibandronate S-Propylene Glycolate by recrystallization

Sodium Ibandronate (2.0 g) was suspended in 6 mL (3.0 vol) of water in a round bottom flask. The flask was heated to dissolution (55-65° C.) at which point 2 mL S-propylene glycol (1.0 vol) was added to the flask. The temperature of the flask was held at 60-65° C. for 2 hours, then cooled to 20-25° C. and held at this temperature for 0.5 hours. Acetone (4 mL, 2.0 vol) was added and the flask was stirred at 20-25° C. for 0.5 hours. The precipitated solid was isolated by filtration, rinsed with acetone and dried in a vacuum oven at 60-65° C. This provided 2.05 grams of Ibandronate sodium S-propylene glycolate.

As many changes can be made to the examples which exemplify the invention without departing from the scope of the invention, it is intended that all matter contained herein be considered illustrative of the invention and not in a limiting sense.

The embodiments of the invention in which an exclusive property or privilege is claimed are as follows:

1. Ibandronate sodium propylene glycolate characterized by a PXRD pattern having characteristic peaks expressed in an angle 2-theta at:

| Angle 2-theta | Intensity % |
| --- | --- |
| 9.7 | 0.24 |
| 11.8 | 0.49 |
| 18.3 | 0.86 |
| 19.4 | 0.57 |
| 19.8 | 0.83 |
| 24.5 | 0.59. |

2. Ibandronate sodium propylene glycolate characterized by PXRD diffractogram as depicted in FIG. 1.

3. Ibandronate sodium propylene glycolate characterized by a PXRD pattern having characteristic peaks expressed in an angle 2-theta at:

| Angle 2-theta | Intensity % |
| --- | --- |
| 9.7 | 0.24 |
| 11.8 | 0.49 |
| 18.3 | 0.86 |
| 19.4 | 0.57 |
| 19.8 | 0.83 |
| 24.5 | 0.59 | and characterized by its IR spectrum (1% KBr) having characteristic peaks expressed in cm$^{-1}$ at:

| IR band (cm$^{-1}$) | % Transmission |
|---|---|
| 3382 | 31 |
| 2385 | 34 |
| 1467 | 42 |
| 1380 | 46 |
| 1162 | 3.2 |
| 1032 | 4.8 |
| 931 | 20. |

4. Ibandronate sodium propylene glycolate characterized by PXRD diffractogram as depicted in FIG. 1, DSC as depicted in FIG. 2, and IR as depicted in FIG. 3.

5. Ibandronate sodium propylene glycolate having a PXRD diffractogram having characteristic peaks expressed in angle 2-theta at 9.7, 11.8, 18.3, 19.4, 19.8 and 24.5.

6. Ibandronate sodium propylene glycolate as claimed in claim 4 when prepared in a manner comprising the steps of:
 a. Dissolving ibandronate sodium in an aqueous medium;
 b. Adding propylene glycol; and
 c. Isolating the resulting solvate by filtration.

7. Ibandronate sodium propylene glycolate as claimed in claim 4 when prepared in a manner comprising the steps of:
 a. Dissolving ibandronate sodium in an aqueous medium, wherein the aqueous medium is in an amount of about 3 volumes of aqueous medium relative to the weight of ibandronate sodium;
 b. Adding propylene glycol in an amount of about 0.5 to 2 volumes of propylene glycol; and
 c. Isolating the resulting solvate by filtration.

* * * * *